United States Patent
Floratos et al.

(10) Patent No.: US 6,341,284 B1
(45) Date of Patent: Jan. 22, 2002

(54) METHOD AND APPARATUS FOR EXHAUSTIVE ENUMERATION OF CORRESPONDENCE IN A SET OF DESCRIPTORS

(75) Inventors: Aris Floratos; Isidore Rigoutsos, both of Astoria; B. David Silverman, Yorktown Heights, all of NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 09/473,318

(22) Filed: Dec. 28, 1999

(51) Int. Cl.⁷ .............................. G06F 17/00
(52) U.S. Cl. .................. 707/6; 707/102; 707/101; 707/501
(58) Field of Search ................. 707/501–513, 707/1–206; 710/107

(56) References Cited

U.S. PATENT DOCUMENTS 599,937 A * 1/1898 Ellard .......................... 707/6
5,970,497 A * 10/1999 Burrows ...................... 707/102
5,978,800 A * 11/1999 Yokoyama et al. ............. 707/6

OTHER PUBLICATIONS

DIVA, Desktop Decision Support for Life Sciences Research; Oxford Molecular Solutions for Discovery Research; DocID 4630 6/99 ©1999 Oxford Molecular Ltd.

* cited by examiner

Primary Examiner—Thomas Black
Assistant Examiner—David Jung
(74) Attorney, Agent, or Firm—Lauren C. Bruzzone

(57) ABSTRACT

The present invention utilizes a set of D descriptors for each of N items. A value K' representing a number of descriptors, and a value K for a number of items that should support an hypothesis are generated, preferably via user input. Collections involving K or more items for which there is an association involving a selection of values across at least K' of the D descriptors are identified, and preferably reported to the user.

26 Claims, 3 Drawing Sheets

METHOD AND APPARATUS FOR EXHAUSTIVE ENUMERATION OF CORRESPONDENCE IN A SET OF DESCRIPTORS

BACKGROUND OF THE INVENTION

1. Field of the Invention

The present invention relates generally to data mining, and, more specifically, to software tools that analyze similarity amongst descriptors of items contained in a database.

2. Description of the Related Art

In a large number of molecular biology tasks descriptors are used to characterize and quantify properties for the item or items of interest. For example in the simplest form of gene expression analysis, a gene's behavior is observed over time and its level of expression tracked as environmental conditions change; many and sometimes all of the genes of a given organism are tracked over time. In the more traditional drug discovery, descriptors (values that characterize structure, charge or other property) for atomic complexes, such as molecules or portions of molecules, form the basis for the selection of potential drug candidates.

Although these are only two examples but they highlight the nature of the problem. Each item of interest (e.g. gene, gene fragment, protein fragment, DNA fragment, atomic complex etc.) is characterized by a set of observable properties (e.g. expression level as a function of a changing environment, shape, mass, inertia, the steric and electrostatics fields it generates, interaction affinity etc.) that are inherently related to its identity or composition. Over the years, various representation schemes have been proposed that attempt to capture and represent some of these observable properties by implicit or explicit calculations carried out on one or more components of the item of interest. As a rule of thumb, there exist no universal representation schemes. Moreover, a given representation scheme typically provides an approximate description of the observable property (-ies) it attempts to capture. For example, and in the general case, the electrostatic field outside of an atomic complex can be described completely with the help of an infinite number of moments (i.e., point charge, dipole, quadrupole, octapole, hexadecapole, and so on); however, low order approximations are typically used that provide a less accurate approximation, but easy to compute.

Given a collection of items of interest (e.g. genes of an organism, gene fragments, protein fragments, DNA fragments, atomic complexes that comprise molecules or molecule fragments) and a representation scheme, the discovery process entails an educated selection among the descriptor set of the items. This selection invariably involves comparisons of and is dependent and based upon the representations that have been chosen for the items under consideration. In the discussion that follows, we will be drawing our examples from the specific problems of gene expression analysis and rational drug design but the described method and system are applicable to any situation where one is given a database of items to be studied with each of the items being represented by a set of descriptors and what is sought is the discovery of collections of items that have values which agree across one or more descriptors.

Software tools have been developed to aid in the discovery process. These tools generally provide the user with the ability to specify a particular descriptor, and then identify the number of items in the set being studied that have the same quantized value for a particular descriptor. In addition, such tools typically provide the user with the ability to specify two or more descriptors, and then identify the number of items in the set being studied that have the same quantized value for the specified descriptors. Alternatively, one can think of the input that such tools process as a two dimensional array of values (the number of rows is equal to the number of items in the database (e.g. genes, gene fragments, protein fragments, DNA fragments, atomic complexes, etc.) while the number of columns is equal to the number of descriptors used by the representation scheme): after one or more columns have been identified, the tool will determine and report to the user those of the database items (e.g. genes, atomic complexes etc.) whose values agree across the entire set of identified columns. Occasionally, the user is also required to specify a minimum support, i.e. the minimum number of atomic complexes that must share the same collection of values across the specified columns. An example of such a tool in the context of rational drug design is DIVA, distributed by Oxford Molecular, additional information regarding this tool may be found at www.oxmol.com. The two-dimensional table relating database items with their attributes is a specific manifestation of what has been called the binary relationship in the context of Galois Concept lattices. A binary relationship consists of explicitly stating the attributes(descriptors) of a group of objects (genes, molecules, etc.). The present work is a unique tool in providing in a most efficient manner the entire hierarchy of descriptor correspondences and the support for each such correspondence. Namely, how many objects (genes, gene fragments, protein fragments, DNA fragments, atomic complexes, etc.) agree with respect to every conceivable subset of descriptor correspondences.

To stress the generality of the problem as we have just defined it, we wish to note that the following database comprising 5 items that are represented using a set of 6 descriptors

| | | | | | | |
|---|---|---|---|---|---|---|
| $s_1 =$ | rent | R&B | romance | BSc | $30K | lexus |
| $s_2 =$ | rent | rock | fiction | MSc | $50K | bmw |
| $s_3 =$ | own | jazz | science-fiction | PhD | $70K | chevy |
| $s_4 =$ | own | jazz | romance | PhD | $70K | dodge |
| $s_5 =$ | rent | R&B | fiction | MSc | $30K | ford | can be equivalently represented

| | | | | | | |
|---|---|---|---|---|---|---|
| $s_1 =$ | 1 | 3 | 6 | 9 | 12 | 15 |
| $s_2 =$ | 1 | 4 | 7 | 10 | 13 | 16 |
| $s_3 =$ | 2 | 5 | 8 | 11 | 14 | 17 |
| $s_4 =$ | 2 | 5 | 6 | 11 | 14 | 18 |
| $s_5 =$ | 1 | 3 | 7 | 10 | 14 | 19 |

$$s_1 = e_1\ e_3\ e_6\ e_9\ e_{12}\ e_{15}$$
$$s_2 = e_1\ e_4\ e_7\ e_{10}\ e_{13}\ e_{16}$$
$$s_3 = e_2\ e_5\ e_8\ e_{11}\ e_{14}\ e_{17}$$
$$s_4 = e_2\ e_5\ e_6\ e_{11}\ e_{14}\ e_{18}$$
$$s_5 = e_1\ e_3\ e_7\ e_{10}\ e_{14}\ e_{19}$$

where $\{e_1, e_2, e_3, e_4, e_5, e_6, e_7, e_8, e_9, e_{10}, e_{11}, e_{12}, e_{13}, e_{14}, e_{15}, e_{16}, e_{17}, e_{18}, e_{19}\}$ are user-defined symbols, without any loss of information. Correspondences discovered on input of this type are typically thought of as associations and the problem of discovering these corresponsdences is also referred to as association discovery.

The problem described above is computationally very demanding and although it is tractable for small collections of database items, its computational requirements become prohibitive very quickly independent on whether the user drives the discovery process or the computer performs a brute force exhaustive enumeration. Let us first examine the case where the user drives the discovery. Every time the user identifies a collection of descriptors of interest the user has made a hypothesis about a potential relationship (i.e. association) among the descriptors. The computational tool will then process the input in order to verify whether the user's hypothesis is supported by the input set. Each hypothesis that is corroborated by the computational tool gives rise to a collection V of atomic complexes that is then examined in order to determine its quality: this can be achieved easily by examining the observable properties of each of the V reported complexes to determine an agreement; if successful, a potential causal relationship is formed that leads from a specific choice of values for the identified set of descriptors to the intersection of observable properties of the respective set of reported database items; the descriptors in the specified set that led to a verified hypothesis are then thought of as being "associated" or "correlated." These formed causal relationships are further analyzed for validity using other means of investigation.

If a hypothesis proves to lead to no such potentially promising results, the user identifies a new collection of descriptors and lets the computational tool repeat the processing. In the absence of any task-specific knowledge, the user would have to repeatedly identify sets of descriptors that the tool will need to process.

As an alternative to the above described process, other currently available methods proceed by a brute force enumeration: collections comprising increasingly more descriptors (one descriptor, two descriptors, three descriptors, etc.) are hypothesized by the computational tool this time (instead of the user) and as above checked to determine whether they are supported by the input set. In other words, instead of the user making a potentially educated selection among the available set of descriptors, the computer enumerates over all possible such selections.

Obviously, and independent of whether it is the user or the computational tool that is driving the descriptor selection process, up to $2^D$ many descriptor choices may have to be made (i.e. choices involving exactly two, three, four, five, ..., D-1, and D descriptors) by the user before any promising result can be reported. Typically, only promising such choices may be made effectively pruning the number of possibilities and speeding up the process. But in the case of a general input these approaches are computationally very demanding.

Because of the evident computational complexity, some of the currently available tools leave the decision process to the user who has to explicitly select the descriptors that are of interest instead of automatically attempting to process the descriptors for the complexes under consideration. It should be noted that the user's selections are typically independent of whether the processed data set supports agreements amongst the selected descriptors.

But even when a collection of C descriptors has been identified that the computational tool indicated as being supported by a subset of the input comprising S database items, it is still not clear whether these C descriptors are the only descriptors that are shared by the S items. In other words, it is unclear whether any of these collections is maximal with respect to the available set of descriptors. It should be stressed that it is important that any reported descriptor collections be maximal both in terms of composition and of length (i.e. no additional descriptors can be found which are shared by the S items under consideration) since only then will they be most specific. The reason for this last requirement is related to the obvious relevance that the most specific collection of descriptors for these S items has in determining a potential causal relationship that leads from a choice of values for some descriptors to shared observable properties.

It should be evident at this point that there remains a need in the art for a mechanism that efficiently generates an extensive and exhaustive list of correspondences (agreements or associations) amongst the descriptors of a set of database items.

SUMMARY OF THE PRESENT INVENTION

The problems stated above and the related problems of the prior art are solved with the principles of the present invention, method and apparatus for exhaustive enumeration of similarity in a set of descriptors. The present invention utilizes a set of D descriptors for each of N items. A value K' representing a number of descriptors, and a value K for a number of items that should support an hypothesis are generated, preferably via user input. Collections involving K or more items for which there is an association involving a selection of values across at least K' of the D descriptors are identified, and preferably reported to the user.

DETAILED DESCRIPTION OF THE INVENTION

Figure 1:
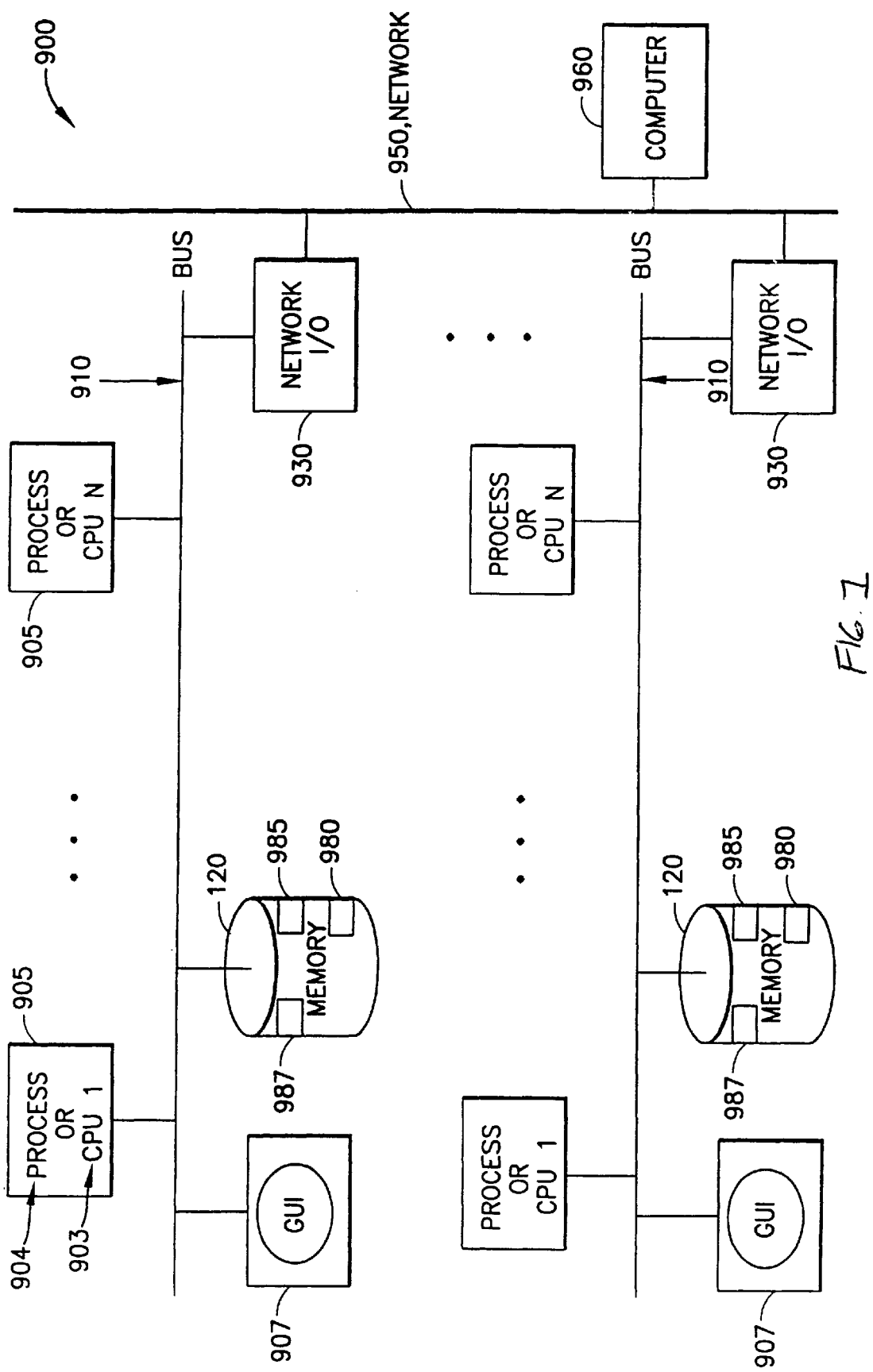
FIG. 1 is a block diagram of a computer processing system wherein the method of the present invention may be embodied.

The present invention may be implemented on any computer processing system including, for example, a personal computer or a workstation. As shown in FIG. 1, a computer processing system 900 as may be utilized by the present invention generally comprises one or more computers or processes. An example of a computer 905 is a central processing unit (CPU) 903 connected to a bus 910 that is further connected to memory 120, a graphical user interface 907 (such as a display), and optionally a network input/output (I/O) device 930. Memory 120 typically includes persistent storage (such as ROM, a hard disk drive, a CD-ROM drive, an optical drive, ROM or other suitable storage device) and non-persistent storage (such as RAM). The operating system and application programs that execute on the CPU 903 are typically stored in persistent storage and loaded into non-persistent storage for execution by the CPU 903. Portions of the operating system and application programs that execute on the CPU may be loaded from network resources into memory 120 via the network I/O device 930. An example of a such a system 900 is the IBM RS/6000 workstation.

It should be noted that the application program(s) executed by the CPU 903 may perform the methods of the present invention described below. Alternatively, portions or all of the methods described below may be embodied in hardware that works in conjunction with the application program executed by the CPU 903.

According to the present invention, data is stored in memory that characterizes a database of items (e.g. collections of genes from one or more organisms, gene fragments, DNA fragments, atomic complexes). More specifically, each item in the database is associated with a unique identifier i and a descriptor vector $V_i$ consisting of an ordered series of D values that characterize the item associated with the unique identifier i. For example, the descriptor vector in the case of a database containing atomic complexes may include components that characterize structure, charge distribution, or some other property of the atomic complex that is of interest. Preferably, the descriptor vectors are stored as part of a file in persistent storage and loaded into non-persistent storage for use by the CPU 903 as needed.

In the case of databases comprising atomic complexes, exemplary descriptor vectors may include values based upon the inertial moments, dipole moments, or molecular weight of a molecule as described in U.S. Pat. No. 5,784,294 to Platt and Silverman, assigned to the assignee of the present invention and herein incorporated by reference in its entirety. In another example, the descriptor vectors may include values based upon the inertial moments, dipole moments, molecular weight of portions of a molecule as described in U.S. Patent (application Ser. No. 09/275,568, filed Mar. 24, 1999, to Pitman et al, commonly assigned to the assignee of the present invention and herein incorporated by reference in its entirety. In these examples, the inertial moments, dipole moments and molecular weights for the set of atomic complexes are calculated as floating point values. It should be noted that neither the nature of the items contained in the processed database nor the descriptor vectors used to represent these items are in any way limiting the present invention. Also, the nature of the descriptors that are used and the techniques that are employed to calculate the data values making up the descriptor vectors of the present invention are arbitrary.

The descriptor vectors are logically partitioned into a matrix of rows and columns. The i-th row represents the ordered set of data values of the descriptor vector $V_i$ which is associated with the i-th database item. The data value present at the j-th column of the i-th row corresponds to the value of the j-th component of the descriptor vector $V_i$.

In addition, the present invention assumes that the data values in a given column are in the most general case real values and lie within a range that is either given or can be computed from the given input data (i.e., a defined interval of values, such as defined range of real numbers). In the event that one or more of the data values of a given descriptor vector $V_i$ do not lie within the defined interval for such data values, these data values are mapped to an out-of-bounds.

Given the allowed range of values for each descriptor component, a mapping of the original values to integers is possible through any of a number of available quantization techniques; for example, the mapping may involve a standard procedure such as uniform binning between the smallest and largest values (potentially with a prior elimination of outliers), frequency based binning, or other. Quantization essentially remaps the original descriptor-component value to the identifier of the quantization bin to which it gets assigned. This assignment of the data values to bins can be automatic, context-specific, or user determined.

As an example, in the case where a descriptor component can assume real (floating point) values, the following method outlines one possible way in which these values can be mapped to a set of integers. First, the floating point values for the descriptor-component under consideration are ordered and the range of floating point values in the column is calculated. Second, the calculated range is divided into a fixed number of bins (which may be equally sized, or which may be variably sized) and each of the descriptor-component values replaced by the identifier of the bin which contains it. The process is repeated for each of the descriptor-components that assume real values. It should be stressed that the descriptor vectors of the present invention need not be limited in this respect, and that the technique that maps the data values making up the descriptor vectors of the present invention can be arbitrary.

In all cases and after all component values have been mapped to integers, they can optionally be mapped once again to a set of symbols or left as integers. Whether this step is performed depends on the number of distinct integers that are needed to represent the values of all descriptor components. It should be noted that the same symbols can be reused to describe values in different columns: indeed, the integer 3 representing a value of the j-th descriptor-component is different than the integer 3 representing a value of the k-th descriptor component because the j-th and k-th components capture two different properties and correspond to potentially different value intervals. As a final comment, it should also be noted that the present technique does not depend on whether this second remapping to symbols takes place or not. For the rest of this description and without loss of generality we will assume that all descriptor values have been mapped to symbols; this assumption will also facilitate the discussion.

In addition, a mechanism is provided that interacts with the user, preferably via graphical user interface 907, to generate constraints K' and K. Preferably, the constraint K' represents a minimum number of columns that must contain matching data values (i.e., data values that match in the symbol space defined for the column), whereas the constraint K represents a minimum number of database items that must contain these matching data values.

Finally, an analysis phase is performed that generates data that exhaustively enumerates subsets of K (or more) atomic complexes whose corresponding data values match in the same K' (or more) columns. Preferably, the data representing the exhaustive list of subsets and the database items in each subset is stored in memory for subsequent use. In addition, the exhaustive list of subsets and the database items in each subset may be reported to the user, preferably via display device 105.

Figure 2:
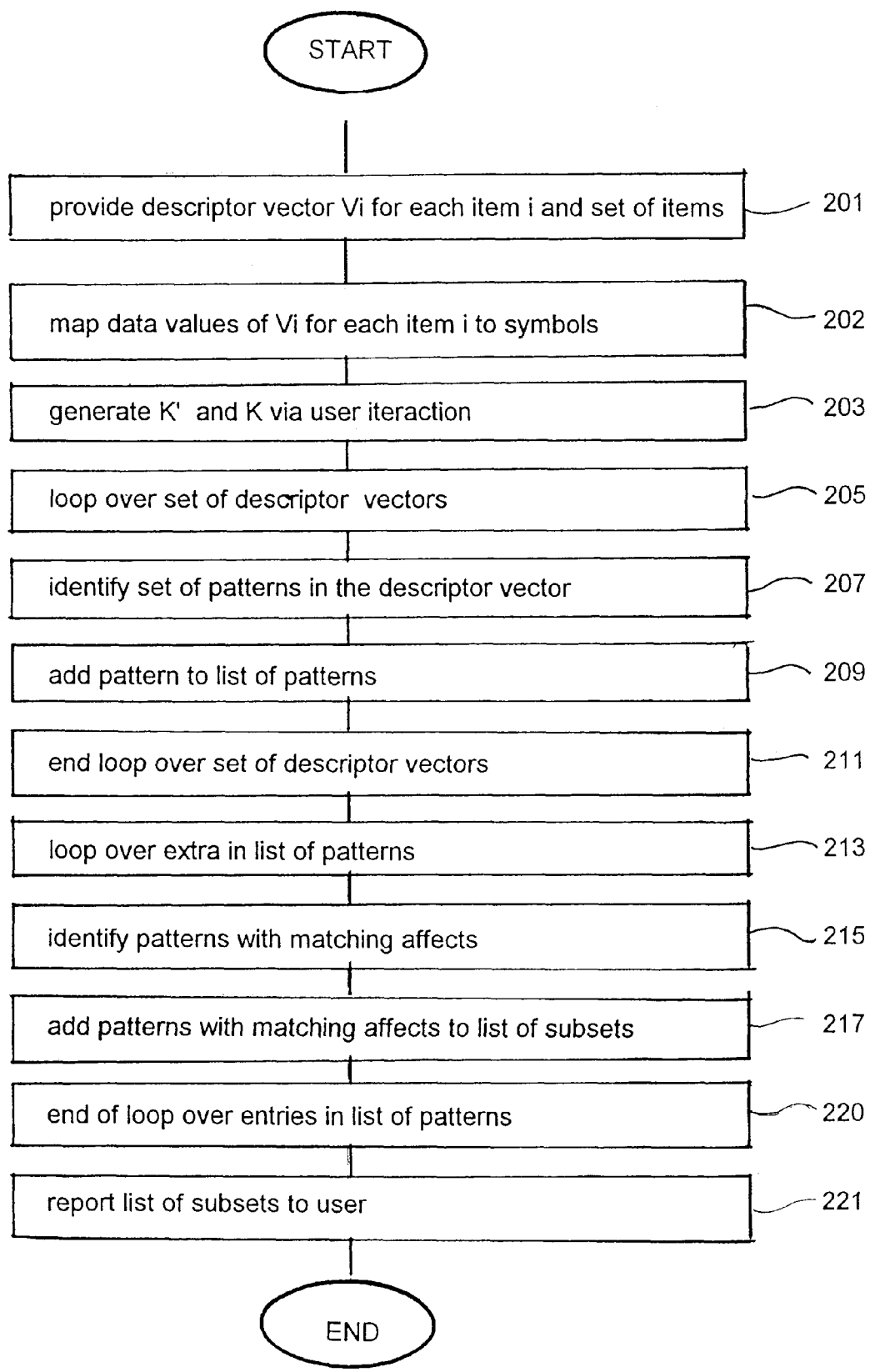
FIG. 2 is a flow chart illustrating the method of the present invention in enumerating correspondence amongst subsets of descriptors in a set of database items (e.g. gene,gene fragment, protein fragment, DNA fragment or molecular descriptor vectors)

An exemplary embodiment of the method of the present invention is illustrated in FIG. 2. In step 201, a descriptor vector $V_i$ for each database item i in a set of database items is provided. Preferably, the descriptor vectors are stored as part of a file in persistent storage and loaded into non-persistent storage for use by the CPU 903 as needed. The descriptor vector $V_i$ consists of an ordered series of D values that characterize the database item associated with the unique identifier i. The descriptor vectors logically form a matrix of rows and columns. Each given row represents the ordered set of data values of the descriptor vector $V_i$ that corresponds to the i-th database item. Each given column represents data values for the corresponding component of the descriptor vectors for the set of database items.

In step 202, the data values of the descriptor vectors are mapped to symbols as described above.

In step 203, user interaction, preferably via graphical user interface 907, generates constraints K' and K. Preferably, the constraint K' represents a minimum number of arbitrary columns that must contain matching data values (i.e., data values that match in the symbol space defined for the column), whereas the constraint K represent a minimum number of database items that must agree on these K' or more columns.

In step 205–211, a loop is performed over the set of descriptor vectors provided in step 201. In step 207, for a given descriptor vector, a set of patterns of symbols (or integers) contained in the given descriptor vector is generated. Such a pattern may be defined as follows. Consider a finite set of symbols $\Sigma=\{c_1, c_2, \ldots, c_n,\}$. The set $\Sigma$ is called an "alphabet" and the elements of $\Sigma$ are interchangeably referred to as symbols or characters. A pattern is defined to be any string over the alphabet $\Sigma \cup \{`.'\}$. The character `.' is assumed to be a special character, not part of $\Sigma$. We differentiate `.' from the characters of $\Sigma$ by referring to `.' as the "don't care" character (or simply "don't care") while the characters of $\Sigma$ are referred to as the "regular" characters. In addition to the regular and don't care symbols, we use bracketed expressions such as [ABCDE] that can contain a minimum of two but not more that $|\Sigma|-1$ regular symbols and indicate that the position they correspond can be occupied by one of the listed regular symbols, in this case one of A or B or C or D or E. Examples of patterns using an English alphabet include:

"A . . [KLM]E" "C . [QN][ST]R . . . RSY" ". . AFG . RT[FG]" "H . . . H ."

among others. A pattern is "present in" an ordered set of symbols (or sometimes referred to as "supported by" the ordered set of symbols) at a given offset (preferably measured from the initial symbol in the ordered set of symbols) when the first regular character of the pattern occurs at the given position in the ordered set of symbols and the other regular characters occur in the same positions in the ordered set of symbols. In other words, the spacing of the regular characters is identified by don't care characters. Thus, the pattern "A . . [KLM]E" is contained in "BIGAPPLE" at an offset of 3.

Preferably, the minimum number of brackets and regular symbols for each pattern generated in step 207 is set to the constraint K' generated in step 203. In addition, the set of patterns generated in step 207 may satisfy additional constraints such as support by a minimum of K atomic complexes, minimum length, maximum length, maximum number of don't care place holders, etc). Such constraints may be set by user input or by the programmer implementing the method of the present invention.

An exemplary method for generating the set of patterns in an ordered set of symbols (step 207) is described in U.S. Patent (U.S. patent application Ser. No. 09/023,756) to Rigoutsos et al., commonly assigned to the assignee of the present invention, herein incorporated by reference in its entirety. This methodology utilizes a set of templates to identify a list of seed patterns in the ordered set of symbols, and utilizes a convolution operation to extend the seed patterns to identify a set of patterns contained in the ordered set of symbols.

Figure 3:
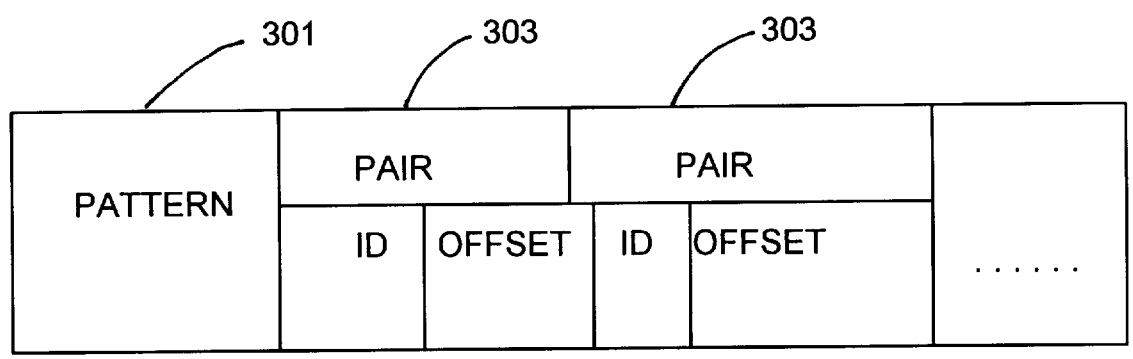
FIG. 3 is a pictorial illustration of an entry in a list of patterns generated by the method of FIG. 2.

In step 209, for each pattern generated in step 207 contained in the given descriptor vector, a entry in a list of patterns is added (or updated). As illustrated in FIG. 3, the entry 300 includes a pattern field 301 that contains (or points to) the pattern, and one or more ID field/offset field pairs 303. The ID field of a given pair 303 identifies the descriptor vector (thus atomic complex) that contains the corresponding pattern (i.e., the pattern of the pattern field 301), and the offset field of the given pair 303 identifies the offset of the corresponding pattern in the descriptor vector identified by the ID field of the pair. The list of patterns is generated in step 209 as follows. For each pattern of symbols generated in step 207, if a given pattern is not found in the list, a new entry is created and initialized with the appropriate data to reflect the occurrence of the pattern in the given descriptor vector. If a given pattern exists in the list, the corresponding entry is updated with the appropriate data to reflect the occurrence of the pattern in the given descriptor vector.

Then, the operation returns to step 205 to process the next descriptor vector in the loop 205–211. When all the descriptor vectors have been processed, the loop 205–211 continues to step 213.

In step 213–219, a loop is performed over the pattern entries in the list of patterns. In step 215, for a given pattern entry 300, the processing identifies all ID field/offset field pairs 303 in the given entry that contains matching offset fields. It should be noted that there may be more than one group of ID field/offset field pairs 303 in the given entry that contains matching offset fields. In step 217, for each group of ID field/offset field pairs 303 that contain matching offset fields as generated in step 215, the pattern field 301 of the entry and the ID fields of the matching ID field/offset field pairs of the entry are added as an entry in a list of subsets stored in memory for subsequent use. After the processing of step 217, the operation returns to step 213 to process the next entry in the loop 213–219. When all the entries in the list of patterns have been processed, the processing of the loop 213–219 ends, and the operation preferably continues to step 221.

It should be noted that at the end of the processing of the loop 213–219, the pattern field and corresponding ID fields of the entries in the list of subsets generated and stored in memory in step 217 exhaustively enumerates all subsets of at least K atomic complexes whose corresponding data values match in the same arbitrary K' (or more) columns.

In step 221, the list of subsets is preferably reported to the user via an output device such as the display system of the computer processing system.

The following illustrates an exemplary dataset where the database items are entire molecules. For each of the 165 molecules in the processed dataset, a total of 14 descriptors is provided. A more detailed description of these 14 descriptors for a given molecule may be found in U.S. Pat. No. 5,784,294 to Platt and Silverman, incorporated by reference above in its entirety. For each molecule in the dataset, each one of the 14 descriptors are mapped to one of 5 bins (denoted by the symbols A, B, C, D and E). This mapping is performed by dividing the range of the data values for the descriptor over the 165 molecules into 5 equally sized bins (although alternative quantization schemes may be used), and mapping the data value for the descriptor to the appropriate bin. For example, this mapping may be performed as follows:

bins A, B, C, D, E are assigned to bin_IDs 0,1,2,3,4 respectively;

_bins is the number of bins; in this example, it is 5;

data_value is the data value of the descriptor to be mapped;

min_value is the minimum data value for the descriptor over the 165 molecules;

max_value is the maximum data value for the descriptor over the 165 molecules;

a function integer(X) accepts as an input a decimal fraction X having an integer portion (to the left of the decimal point) and a fractional portion (to the right of the decimal point) and outputs the integer portion of X;

bin_ID=integer(((data_value−min_value)/(max_value−min_value))*(#_bins−1))

Each 14-element descriptor vector (in symbol space) is preceded by 'b' (for beginning) and followed by 'e' (for end), for ease of description.

>molecule_id=1
bABABCAACCCBCADe
>molecule_id=2
bAABADADBCCBAEDe
>molecule_id=3
bBABBCBCBCCBBCDe
>molecule_id=4
bBAABABABBBABACe
>molecule_id=5
bAABABCBBBBABACe
>molecule_id=6
bBAAAABBBBCACACe
>molecule_d=7
bAABABCBBBBACACe
>molecule_d=8
bAADBBBBBBBABACe
>molecule_id=9
bAAAACAABCCCCACe
>molecule_id=10
bABAADABBCCABADe
>molecule_id=11
bBAAABBBBCCBCBCe
>molecule_id=12
bAACABBBBCCABACe
>molecule_id=13
bAAAAABBBCCEBADe
>molecule_id=14
bCAABABABBBAAACe
>molecule_id=15
bAAAAABABBBABBCe
>molecule_id=16
bBBDBDABBBBABACe
>molecule_id=17
bBACBBCBBBBABACe
>molecule_id=18
bAACBEAEBCCBACDe
>molecule_id=19
bBABBABBCCCABBDe
>molecule_id=20
bBBBBCBBCCCAABDe
>molecule_id=21
bAADACACBBBAAACe
>molecule_id=22
bBABAABBCCCBAADe
>molecule_id=23
bBAABABBDEEABCEe
>molecule_id=24
bBABBCBBBCCBABDe
>molecule_id=25
bBAABABACCCBCADe
>molecule_id=26
bBAABABABBBAAACe
>molecule_id=27
bABAADAACCCBDADe
>molecule_id=28
bAAAABBABCCBDBDe
>molecule_id=29
bAAAABBABCCCEBCe
>molecule_id=30
bBACBBBBCDDAAADe
>molecule_id=31
bBADBBBBCDDAAADe
>molecule_id=32
bACABACBAAAAAABe
>molecule_id=33
bACABACBAAAAAAe
>molecule_id=34
bBAABABBAAAAAAAe
>molecule_id=35
bBBABACBAAAAAAAe
>molecule_id=36
bBBABABBAAAAAAAe
>molecule_id=37
bACABACBAAAAAAAe
>molecule_id=38
bACABACBAAAAAAAe
>molecule_id=39
bACABACBAAAAAAAe
>molecule_id=40
bACABACBAAAAAAAe
>molecule_id=41
bACABACBAAAAAAAe
>molecule_id=42
bACABACBAAAAAAAe
>molecule_id=43
bACABACBAAAAAAAe
>molecule_id=44
bBCABABAAAAAAAAe
>molecule_id=45
bABAAACBAAAAAAAe
>molecule_id=46
bABAAACBAAAAAAAe
>molecule_id=47
bAAAAACBAAAABAAe
>molecule_id=48
bABAAACBAAAAAABe
>molecule_id=49
bABAAACBAAAAAABe
>molecule_id=50
bAAAAACBAAAABAAe
>molecule_id=51
bABAAACBAAAAAABe
>molecule_id=52
bABABABBAAAAAAAe
>molecule_id=53
bAAAAACBAAAAAAAe
>molecule_id=54
bABAAABBAAAAAACe
>molecule_id=55
bAAAAABBAAAABAAe
>molecule_id=56
bBBABABBAAAAAABe
>molecule_id=57
bAAAAACBAAAAAABe
>molecule_id=58 bAAAAABBAAAABAAe
>molecule_id=59
bAABAACAAAAAAAAe
>molecule_id=60
bAAAAACBAAAAAABe
>molecule_id=61
bAAAAACBAAAAAABe
>molecule_id=62
bAAAAACBAAAAAABe
>molecule_id=63
bAAAAACBAAAABABe
>molecule_id=64
bAAAAABBBABAAACe
>molecule_id=65
bABBAACAAAAAAABe
>molecule_id=66
bABBAACAAAAAAABe
>molecule_id=67
bABBAACAABBAAACe
>molecule_id=68
bAAAAACBAAAABAAe
>molecule_id=69
bBBEBACABBBAAACe
>molecule_id=70
bBBCBABAAAAAAABe
>molecule_id=71
bBBDBACAAAAAAABe
>molecule_id=72
bAAAAABAAAAABABe
>molecule_id=73
bAAAAABAAAAABABe
>molecule_id=74
bAAAAACBAAAABAAe
>molecule_id=75
bAAAAABAAAAABABe
>molecule_id=76
bAAAAABAAAAAAAe
>molecule_id=77
bAAAAABBAAAAAAAe
>molecule_id=78
bAAAAABAABBABACe
>molecule_id=79
bAAAAABAABBABACe
>molecule_id=80
bBAABABAAAAAAABe
>molecule_id=81
bAAAAABAABAABABe
>molecule_id=82
bAAAAABAAAABDAAe
>molecule_id=83
bAABAACBAAAAAAAe
>molecule_id=84
bAAAAACBAAAAAABe
>molecule_id=85
bAAAAACBAAAABABe
>molecule_id=86
bAABAABAABBAAABe
>molecule_id=87
bAAAAACBAAAABABe
>molecule_id=88
bAAAAABAABBABACe
>molecule_id=89
bAABAABAABBAAABe
>molecule_id=90
bAABAABAAAAAAABe
>molecule_id=91
bAACAABAABBAAACe
>molecule_id=92
bAAAAACBAAAABAAe
>molecule_id=93
bBBABACBABBAAACe
>molecule_id=94
bBABBABAAAAAAABe
>molecule_id=95
bBADBACAAAAAAAe
>molecule_id=96
bBAABBCCABBABABe
>molecule_id=97
bBBABCCCBBBABACe
>molecule_id=98
bBAABCCCBBBAAACe
>molecule_id=99
bABAAACBABBAAABe
>molecule_id=100
bABAAACBABBAAABe
>molecule_id=101
bABAAACBACCAAACe
>molecule_id=102
bABCBACBAAAAAABe
>molecule_id=103
bABAAACBABBAAABe
>molecule_id=104
bAAAABCCACCABACe
>molecule_id=105
bAAAAABBABBABABe
>molecule_id=106
bBBABCCCBBBAAACe
>molecule_id=107
bBBABCCCBBCAAACe
>molecule_id=108
bBAABCCCBBCAAACe
>molecule_id=109
bBAABCCCBBBAAACe
>molecule_id=110
bBAABCCCBBBAAACe
>molecule_id=111
bBBBBCCCBBBAAACe
>molecule_id=112
bBBABCCCBBBAAACe
>molecule_id=113
bAAAABBCBBBABACe
>molecule_id=114
bBAAABCBAAAABABe
>molecule_id=115
bBBABBCCBBCABACe
>molecule_id=116
bADACACBBBBAAACe
>molecule_id=117
bACBBBCBBBBAAACe
>molecule_id=118
bBDACACBBBBAAACe
>molecule_id=119 bBBABBCCBBBAAACe
>molecule_id=120
bDAACABBBBBAAACe
>molecule_id=121
bEAADABBBCCAAACe
>molecule_id=122
bDBACBBCBCCABACe
>molecule_id=123
bAAAACCCBBCAAACe
>molecule_id=124
bBBABCCCBBCAAACe
>molecule_id=125
bBAABBBBAAAAAABe
>molecule_id=126
bDCAEABBABBAAABe
>molecule_id=127
bBBABCCCBCCABACe
>molecule_id=128
bBAABBBCBBBABACe
>molecule_id=129
bABAAACBAAAABABe
>molecule_id=130
bABAABCBAAAABABe
>molecule_id=131
bACABABBBBBABACe
>molecule_id=132
bBCABBCBBBBAAACe
>molecule_id=133
bACABCDBDBCACACe
>molecule_id=134
bACABBDBCBBAAACe
>molecule_id=135
bACABBCBCBBABACe
>molecule_id=136
bABAABCBDBBADACe
>molecule_id=137
bABAAABBCBBAAACe
>molecule_id=138
bBDACBCBCABAAACe
>molecule_id=139
bADBCBCBCBBAAACe
>molecule_id=140
bACABBCBEBBACADe
>molecule_id=141
bADABACBDBCAAADe
>molecule_id=142
bACABBDBBBBABACe
>molecule_id=143
bADBCBDBCBBAAACe
>molecule_id=144
bBDACBCBCBBAAACe
>molecule_id=145
bADACBDBCBBABACe
>molecule_id=146
bADBBACBCBCABACe
>molecule_id=147
bADACBDBCBBABACe
>molecule_id=148
bABABABACCCAAACe
>molecule_id=149
bADABACBDCCABADe >molecule_id=150
bADACBDBCBBAAACe
>molecule_id=151
bACABCEBDBCACADe
>molecule_id=152
bABBBABACCCAAACe
>molecule_id=153
bADBBACBDCCABADe
>molecule_id=154
bADBBACBCBCABACe
>molecule_id=155
bADACBDBCBBAAACe
>molecule_id=156
bACBBBDBBABABACe
>molecule_id=157
bBDBCBCBBBBAAACe
>molecule_id=158
bACABBCBBBBABACe
>molecule_id=159
bADACCDBCBBAAACe
>molecule_id=160
bACABBDBBBBABACe
>molecule_id=161
bAEACBDBCBBAAACe
>molecule_id=162
bACABBDBBBBABACe
>molecule_id=163
bACBBACBDBCABACe
>molecule_id=164
bABBBACBCBBAAACe
>molecule_id=165
bACABBDBCBBAAACe Here we are showing an example of different patterns that have support 9, there is a total of 9 atomic complexes (molecules) that exhibit the correspondences shown. Each of the reported patterns has been rewritten to indicate those of the wild card characters ('.') that could be dereferenced using 2 bin choices.

| # of molecules that support | pattern | molecule_ID of molecules exhibiting correspondence |
|---|---|---|
| 9 | b..A....BCC....e | 8, 9, 10, 12, 27, 28, 120, 121, 126 |
|  | b.[AB]A....BCC....e |  |
| 9 | b.B..A...AAAAAABe | 47, 48, 50, 55, 64, 65, 69, 70, 101 |
|  | b[AB]B.[AB]A[CB]AAAAAABe |  |
| 9 | b....AB...BAAA.e | 13, 25, 63, 85, 88, 90, 119, 125, 136 |
|  | b....AB[AB].[BA]BAAA.e |  |
| 9 | b....A..C......e | 18, 21, 24, 136, 145, 147, 151, 153, 163 |
|  | b[AB].[BA][BA]A[BC][BA]C[CB][CB]....e |  |
| 9 | b..A...BBBBA.ACe | 115, 117, 119, 130, 131, 141, 157, 159, 161 |
|  | b..A[BC]6[BA].BBBBA[BA]ACe |  |
| 9 | bA.A.A...BBA.A.e | 77, 87, 98, 99, 102, 104, 115, 130, 136 |
|  | bA.A.A[BC][BA].BBA[AB]A.e |  |
| 9 | bBA.B....B.A.A.e | 3, 16, 25, 95, 97, 107, 108, 109, 127 |
|  | bBA[AC]B.[CB].7[BA]B[BC]A[AB]A.e |  |
| 9 | bA...A...BBA..Ce | 14, 66, 77, 87, 90, 115, 130, 136, 163 |
|  | bA...A[BC][AB].BBA[AB][AB]Ce |  |

-continued

| # of molecules that support | pattern | molecule_ID of molecules exhibiting correspondence |
|---|---|---|
| 9 | bA.A...B..BAAACe | 63, 115, 133, 136, 149, 154, 158, 160, 164 |
| | bA.A...B7[CB][BA]BAAACe | |
| 9 | bA..AA....BAAA.e | 63, 66, 85, 88, 90, 98, 99, 102, 136 |
| | bA[BA].AA[BC][BA].[BA]BAAA.e | |
| 9 | bA.AAACBAAAABA.e | 46, 49, 62, 67, 73, 84, 86, 91, 128 |
| | bA[AB]AAACBAAAABA.e | |
| 9 | b.A..AC.AAAAAA.e | 52, 56, 58, 59, 60, 61, 82, 83, 94 |
| | b[AB]A.[AB]AC[BA]AAAAAA.e | |
| 9 | bA.A....B...B..e | 9, 12, 14, 112, 130, 141, 157, 159, 161 |
| | bA.A[BA]...B[BC][BC]4[AE]B..e | |
| 9 | b..B...B....A..e | 19, 21, 23, 82, 116, 138, 142, 156, 163 |
| | b[AB].B...B...4[AB]A..e | |
| 9 | b..A.B....BAAACe | 118, 131, 133, 137, 143, 149, 154, 160, 164 |
| | b[AB].A[CB]B[DC][BC]7[CB][BA]BAAACe | |

Thus, the present invention provides an efficient methodology for enumerating a complete list of database-item-collections (atomic complexes in the above example) that share the same (quantized or not) value across one or more descriptors. Unlike the currently available methods, the presented method is efficient because it relies on pattern discovery to determine these collections instead of brute-force enumeration. Although it is seemingly an equally hard problem, there have been recently described methods for carrying out pattern discovery (for example: one such method is described in U.S. patent application Ser. No. 09/023,756 to Rigoutsos et al., commonly assigned to the assignee of the present invention, and herein incorporated by reference in its entirety) that quarantee that all patterns contained in a database of items will be reported, that such patterns are maximal in both composition and length (see above for a definition) and that do not necessitate a brute-force enumeration of the potential solution space in order to produce their results. Moreover, it has been shown that the method described in the above mentioned U.S. patent application Ser. No. 09/023,756 to Rigoutsos et al. is output-sensitive and that its time complexity is a quasi-linear function of the size of the processed database. What this means in practical terms is that for a given processed database the method will not take more time that it is necessary: if the number of patterns is small (resp. large) the required time to discover and report them will be small (resp. large) thus making it an ideal tool for use in the context of the method that we describe in this invention.

This methodology may be used to efficiently identify those subsets that relate to a particular atomic complex of interest (or particular group of atomic complexes). More specifically, a particular atomic complex of interest (or particular group of atomic complexes) may be identified, preferably via user interaction with a graphical user interface. The list of subsets may be culled to identify those subsets whose associated ID fields include an ID field that matches the particular database item of interest (or particular group of database items). Finally, the matching subsets are preferably reported to the user via an output device such as the display system of the computer processing system.

Alternatively, the list of subsets generated by the method of the present invention as described above may be used to efficiently identify those database items that relate to a particular pattern (or a particular group of patterns). More specifically, a particular pattern of interest (or particular group of patterns) may be identified, preferably via user interaction with a graphical user interface. The list of subsets may be culled to identify those subsets whose associated pattern field corresponds to the particular pattern of interest (or particular group of patterns). Finally, the matching subsets are preferably reported to the user via an output device such as the display system of the computer processing system.

With this tool the user has the ability to immediately identify all sets of database items within an extensive database that exhibit a particular set of correspondences. When obtaining information from an external procedure that identifies those descriptors responsible for a particular activity of interest (e.g. physio-chemical, biological, etc.) the user can immediately identify the set of database items that not only exhibit the appropriate ranges of values of the identified descriptors but also those sets of database items with values that neighbor the identified values. All the data necessary to identify database items associated with every possible range of descriptor values has been catalogued and reported (as part of the discovery process) and therefore the exhaustive enumeration provides a convenient source of immediate information for the user.

It has already been stressed that the present invention is not only applicable to finding similarity amongst descriptors of atomic (molecular) complexes, genes, gene fragments, protein fragments, or DNA fragments. It should to be evident to those skilled in the art that the present invention can be applied to arbitrary collections of descriptors for any arbitrary item of interest. For example, the items of interest may be patients, and the descriptors comprise clinical data that characterizes the medical condition and treatment of the such patients. In another example, the items of interest may be consumers, and the descriptors comprise market data that characterizes the spending and purchasing patterns of such consumers. In all of these examples, the present invention provides the user with the ability to identify all sets of items within an extensive database that exhibit a particular set of correspondences.

While the invention has been described in connection with specific embodiments, it will be understood that those with skill in the art may develop variations of the disclosed embodiments without departing from the spirit and scope of the following claims.

We claim:

1. In a data processing system that includes a database storing information characterizing a plurality of items, a method for generating and storing data characterizing said items, the method comprising the steps of:

providing a plurality of descriptor vectors associated with said plurality of items, wherein each descriptor vector comprises an ordered series of data values associated with one of said plurality of items, wherein said ordered series of data values is logically partitioned into rows and columns, wherein a given row represents data values of a descriptor vector associated a specific item, and wherein a given column represents corresponding data values of said descriptor vectors for each item in said plurality of items;

interacting with a user to generate a first constraint K1 that represents a number of arbitrary columns;

generating data that enumerates subsets of items complexes whose corresponding data values match in the same K1' columns, wherein K1' is based upon the first constraint K1.

2. The method of claim 1, wherein said items comprise one of genes, gene fragments, protein fragments, and DNA fragments.

3. The method of claim 1, wherein the first constraint K1 represents a minimum number of arbitrary columns that must contain matching data values, and wherein K1' is a number that is greater than or equal to the first constraint K1.

4. The method of claim 3, further comprising the step of interacting with a user to generate a second constraint K2 that represents a minimum number of items in a given subset.

5. The method of claim 4, wherein said data exhaustively enumerates all subsets of items that:

i) comprise at least K2 items; and ii) comprise corresponding data values that match in the same K1' columns.

6. The method of claim 1, wherein said data is reported to said user.

7. The method of claim 1, wherein the data values are generated by quantizing real numbers that characterize said items.

8. The method of claim 7, wherein the data values of a given descriptor vector comprise an ordered set of symbols.

9. The method of claim 8, further comprising the step of storing a plurality of pattern entries each including a pattern field identifying a pattern of symbols and at least one ID field/offset field pair, wherein the ID field of a given pair identifies the descriptor that contains the corresponding pattern of the pattern field, and wherein the offset field of the given pair identifies the offset of the corresponding pattern in the descriptor vector identified by the ID field of the pair.

10. The method of claim 8, wherein the generating step utilizes a set of templates to identify a list of seed patterns in the ordered set of symbols for a given descriptor vector.

11. The method of claim 10, wherein the generating step utilizes a convolution operation to extend the seed patterns to identify a set of patterns contained in the ordered set of symbols.

12. The method of claim 1, wherein each of said items comprise an atomic complex.

13. The method of claim 12, wherein each of said items comprise a portion of a molecule.

14. A program storage device for use in a data processing system that includes a database storing information characterizing a plurality of items, the program storage device readable by a machine, tangibly embodying a series of instructions executable by the machine to perform method steps for generating and storing data characterizing said items, the method steps comprising:

providing a plurality of descriptor vectors associated with said plurality of items, wherein each descriptor vector comprises an ordered series of data values associated with one of said plurality of items, wherein said ordered series of data values is logically partitioned into rows and columns, wherein a given row represents data values of a descriptor vector associated a specific item, and wherein a given column represents corresponding data values of said descriptor vectors for each item in said plurality of items;

interacting with a user to generate a first constraint K1 that represents a number of arbitrary columns;

generating data that enumerates subsets of items whose corresponding data values match in the same K1' columns, wherein K1' is based upon the first constraint K1.

15. The program storage device of claim 14, wherein the first constraint K1 represents a minimum number of arbitrary columns that must contain matching data values, and wherein K1' is a number that is greater than or equal to the first constraint K1.

16. The program storage device of claim 15, further comprising the step of interacting with a user to generate a second constraint K2 that represents a minimum number of items in a given subset.

17. The program storage device of claim 16, wherein said data exhaustively enumerates all subsets of items that:

i) comprise at least K2 items; and ii) comprise corresponding data values that match in the same K1' columns.

18. The program storage device of claim 14, wherein said data is reported to said user.

19. The program storage device of claim 14, wherein the data values are generated by quantizing real numbers that characterize said items.

20. The program storage device of claim 19, wherein the data values of a given descriptor vector comprise an ordered set of symbols.

21. The program storage device of claim 20, further comprising the step of storing a plurality of pattern entries each including a pattern field identifying a pattern of symbols and at least one ID field/offset field pair, wherein the ID field of a given pair identifies the descriptor that contains the corresponding pattern of the pattern field, and wherein the offset field of the given pair identifies the offset of the corresponding pattern in the descriptor vector identified by the ID field of the pair.

22. The program storage device of claim 20, wherein the generating step utilizes a set of templates to identify a list of seed patterns in the ordered set of symbols for a given descriptor vector.

23. The program storage device of claim 22, wherein the generating step utilizes a convolution operation to extend the seed patterns to identify a set of patterns contained in the ordered set of symbols.

24. The program storage device of claim 14, wherein each of said items comprise a an atomic complex.

25. The program storage device of claim 24, wherein each of said items comprise a portion of a molecule.

26. The program storage device of claim 14, wherein said items comprise one of genes, gene fragments, protein fragments, and DNA fragments.

* * * * *